United States Patent [19]

Fentress

[11] Patent Number: 5,495,856

[45] Date of Patent: Mar. 5, 1996

[54] MOISTURE BARRIER FOR INDWELLING CATHETERS AND THE LIKE

[75] Inventor: Philip W. Fentress, Memphis, Tenn.

[73] Assignee: Tabex Industries, Inc., Memphis, Tenn.

[21] Appl. No.: 142,373

[22] PCT Filed: May 20, 1992

[86] PCT No.: PCT/US92/04239

§ 371 Date: Nov. 23, 1993

§ 102(e) Date: Nov. 23, 1993

[87] PCT Pub. No.: WO92/21394

PCT Pub. Date: Dec. 10, 1992

Related U.S. Application Data

[63] Continuation-in-part of Ser. No. 706,937, May 29, 1991, Pat. No. 5,230,350.

[51] Int. Cl.[6] .............................. A61F 5/37; A61M 5/00
[52] U.S. Cl. ...................... 128/846; 604/263; 604/307; 604/361
[58] Field of Search ................... 73/52; 206/204; 128/846, 849–856, 872, 888, 889; 602/41–43, 48, 54; 604/111, 174–186, 263, 304, 307, 308, 361, 261, 192, 162, 163, 318

[56] References Cited

U.S. PATENT DOCUMENTS

4,659,329  4/1987  Annis ........................... 604/180

Primary Examiner—Michael A. Brown
Attorney, Agent, or Firm—Susan Fentress

[57] ABSTRACT

A moisture barrier includes inner and outer moisture resistant layers. A moisture absorbing material occupies the region between the two layers. The peripheral edges of the inner and outer layers adhere to the intended surface surrounding the protected area. The adhered edge of the outer layer is spaced from the adhered edge of the inner layer, forming a gap between them. The gap communicates with the open region that contains the moisture absorbing material. The gap presents a path that diverts moisture away from adjoining portions of the seal and toward the moisture absorbing material. Preferably, the moisture absorbing material displays different visible characteristics, depending upon the presence or absence of moisture. The moisture sensing material is positioned for viewing through a light-transmissive portion of the outer barrier layer. The moisture barrier serves to affirmatively keep moisture away from a protected area. The moisture barrier can also serve to immediately notify the user when unwanted invasion of moisture threatens the protected area.

30 Claims, 4 Drawing Sheets

MOISTURE BARRIER FOR INDWELLING CATHETERS AND THE LIKE

RELATED APPLICATIONS

This application is a continuation-in-part of co-pending application Ser. No. 07/706,937, filed May 29, 1991, now U.S. Pat. No. 5,230,350.

FIELD OF THE INVENTION

In a general way, my invention relates to moisture proof barriers. In a more specific sense, my invention relates to barriers that serve to cover and protect areas of the human body where exposure to moisture poses the risk of infection, such as around surgically implanted, indwelling catheters.

BACKGROUND OF THE INVENTION

Today, many people rely upon surgically implanted, indwelling catheters for their health and well being. For example, many diabetic patients use indwelling subclavian catheters for delivering insulin. Patients undergoing long term chemotherapy also may have an indwelling catheter. All peritoneal dialysis patients use an indwelling peritoneal catheter for delivering dialysis fluid.

Protection of the catheter exit site is a significant daily task for these people. Infection of the catheter exit site must be avoided to prevent unintended removal and replacement of the catheter.

People with indwelling catheters often face restrictions on everyday activities that expose the catheter exit site to moisture, such as bathing and swimming. They must take steps to prevent exposing the exit site to moisture. Moisture can support the growth of harmful or infectious bacteria in and around the exit site.

Some people try to protect the catheter exit site against moisture when bathing or swimming by using makeshift plastic covers taped over the exposed end of the catheter. These makeshift covers often fail to work, allowing moisture to enter the catheter exit site. They are not designed to affirmatively repel or divert moisture away from the exit site. Usually, the person does not even know whether leakage has occurred until it is too late. These makeshift covers are simply inadequate to protect the exit site against moisture and the risk of serious infection.

I believe a real need exists for a moisture proof barrier for use by people who must use indwelling catheters or who are otherwise required to take positive steps to protect areas of their bodies against infection due to exposure to moisture.

SUMMARY OF THE INVENTION

My invention meets this and other needs. It provides a moisture barrier that affirmatively keeps moisture away from body areas that must be protected against infection. My invention also provides a moisture barrier that immediately notifies the user when unwanted invasion of moisture threatens the protected area.

One aspect of my invention provides a moisture barrier that is attached to the skin by a seal having an exterior region and an interior region separated by a small gap. The gap provides an alternative fluid path to moisture invading the exterior region of the seal. The gap diverts the unwanted moisture away from the interior region of the seal, thereby keeping the critical area the barrier serves to protect free of moisture.

In one embodiment, this aspect of my invention provides a barrier that includes an inner moisture resistant layer that covers the area to be protected. An outer moisture resistant layer overlies the inner layer, forming an open region between them. A moisture absorbing material occupies this open region.

The peripheral edges of the inner and outer layers adhere to the region surrounding the protected area. The adhered edge of the outer layer is spaced away from the adhered edge of the inner layer, forming a gap between them. The intermediate gap communicates with the open region that contains the moisture absorbing material.

Together, the two adhered edges form a seal that impedes the passage of moisture to the protected area. The intermediate gap interrupts this seal. The gap presents an alternative fluid path to moisture that breaches the outer region of the seal. The gap leads the unwanted moisture to the moisture absorbing material, diverting it away from the inner region of the seal next to the critical area that barrier serves to protect. In this way, the interior protected region is kept free of moisture, even if unintended peripheral leakage of moisture occurs.

Another aspect of my invention provides a moisture barrier that immediately warns the user when unwanted moisture threatens the critical protected area.

In one embodiment, this aspect of my invention provides a barrier that includes a moisture resistant body forming an interior region that overlies the protected area. Adhesive on the peripheral edge of the body adheres the body to the intended area. The adhesive forms a seal that impedes the passage of moisture into the interior protected region.

My invention provides a light-transmissive pocket in the moisture resistant body and places a moisture sensing material inside this pocket. The moisture sensing material is positioned to contact moisture invading the seal. The moisture sensing material displays one visible characteristic when moisture is present and another visible characteristic when moisture is not present. The user can see these visible characteristics through the light-transmissive pocket. The user knows immediately when unwanted moisture has penetrated the seal, threatening the protected area. The user then knows that it is time to replace the barrier.

A preferred embodiment combines both aspects of my invention. It provides a barrier having a moisture sensing material that warns the user when moisture penetrates the seal. The moisture sensing material also serves to absorb the invading moisture. So, the barrier not only visually warns the user when leakage occurs, but it also takes affirmative steps to help the user by absorbing the unwanted leakage.

My invention is well suited for use in the medical field, where the barrier also can include an antimicrobial material in the interior protected region.

The barrier that embodies the features of my invention meets the present need for a moisture proof protective cover for the exposed end of an indwelling catheter. It also can serve as a protective barrier in other environments where exposure to moisture is to be minimized or avoided.

Other features and advantages of my invention will become apparent upon review of the following description, drawings, and appended claims.

DESCRIPTION OF THE PREFERRED EMBODIMENTS

FIGS. 1 to 5 show one embodiment of a moisture barrier 10 that incorporates the features of my invention.

Figure 1:
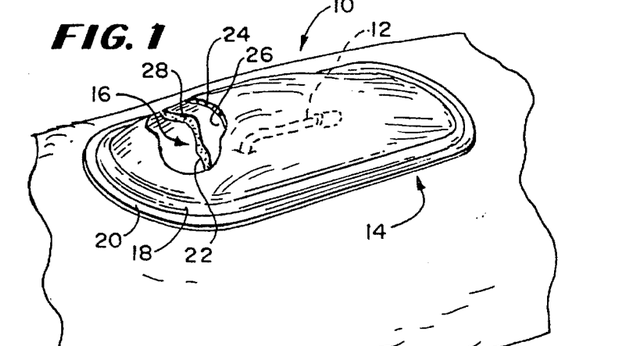
FIG. 1 is a perspective top view, partially broken away and in section, of a moisture barrier for an indwelling catheter that embodies the features of my invention, the barrier being in place on the skin of the user over the catheter exit site.
Figure 2:
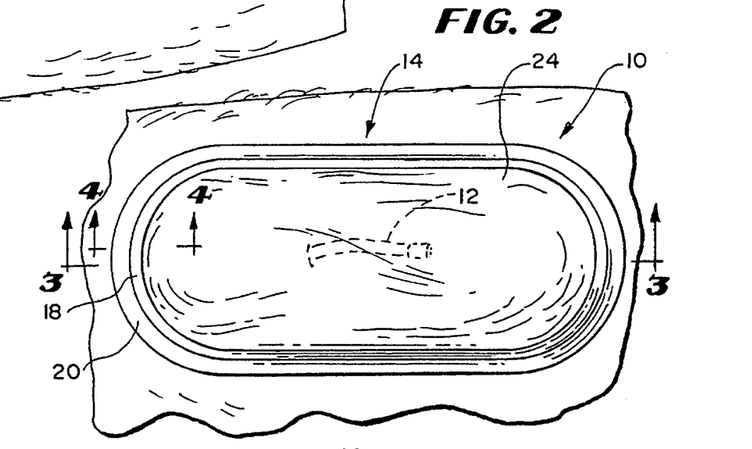
FIG. 2 is a top plan view of the barrier shown in FIG. 1.
Figure 3:
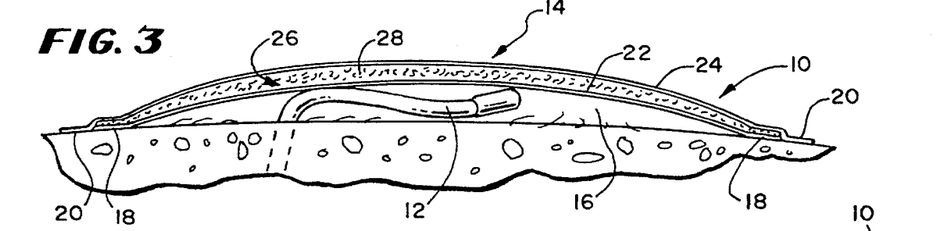
FIG. 3 is a side section view of the barrier taken generally along line 3—3 in FIG. 2.

The barrier 10 is applicable for use in different environments. In this Specification, the barrier 10 will be described as used to cover and protect the exit site of an indwelling catheter 12 (as best shown in FIG. 3). The barrier 10 is particularly well suited for use in this and other environments where the prevention of infection is an important objective.

In this embodiment, the barrier 10 includes a moisture resistant body 14 having an interior protected region 16. At least one peripheral edge that adheres to the skin surrounds the protected area 16. FIGS. 1 to 5 show the body 14 as oval in shape. Of course, the body 14 can be square, rectangular, circular, or almost any selected shape.

In the illustrated embodiment (as FIG. 3 best shows), a series of two adhered edges 18 and 20 surround the interior protected region 16. As will be described later in greater detail, the edges 18 and 20 form an interrupted seal area that impedes the ingress of unwanted moisture into the protected region 16.

In the illustrated embodiment, the barrier body 14 comprises two moisture resistant barrier layers 22 and 24. The first moisture resistant barrier layer 22 directly overlies the interior protected region 16. The barrier layer 22 is preferably preformed in a dome shape (see FIG. 3) to envelop the exposed catheter end 12.

The second moisture resistant barrier layer 24 overlies the first barrier layer 22. A second interior region or pocket 26 extends between the two barrier layers 22 and 24. According to one aspect of my invention, a moisture absorbing material 28 occupies the region 26 between the inner and outer barrier layers 22 and 24.

The first and second barrier layers 22 and 24 can be made of various materials. For example, the layers 22 and 24 can be made of commercially available plastic film, or commercially available Gore-Tex (Trademark) material, or commercially available metallized plastic film, or commercially available foil.

The moisture absorbing material 28 can comprise conventional absorbent paper, fiber, or cloth materials, like those used in conventional reusable and disposable diapers and the "super-absorbent" diapers or tampons. The material 28 also could include conventional agents that trap, stabilize, or otherwise complex the moisture into a non-mobile form.

Figures 4, 5:
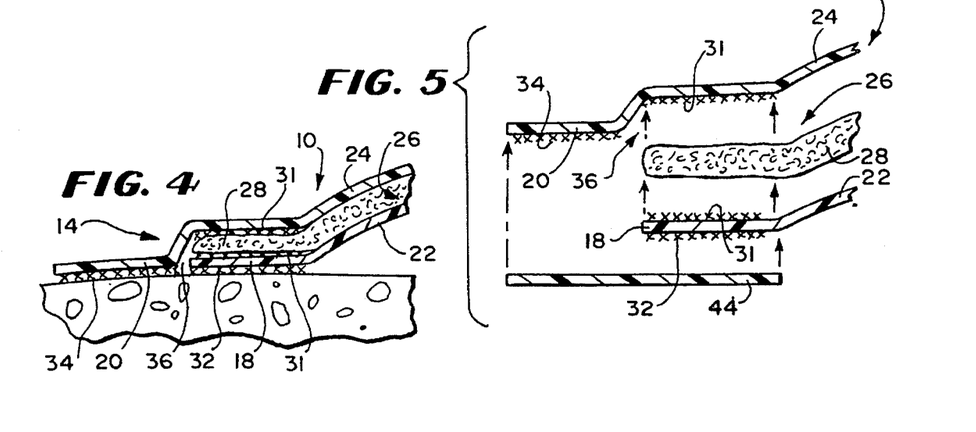
FIG. 4 is a side section view of the peripheral edge of the barrier taken generally along line 4—4 in FIG. 2.
FIG. 5 is an enlarged exploded view of the peripheral edge of the barrier shown in FIG. 4.

As FIG. 5 shows, conventional moisture resistant adhesives 31 can be used to bond the layers 22 and 24 to the peripheral edge of the material 28, thereby forming the composite body 14. For example, Double Coated Tape (Type 1522) made by 3M Corporation could be used as the adhesive 31.

The first barrier layer 22 also includes a conventional moisture resistant adhesive coating 32 about the underside of its peripheral edge 18. The adhesive coating adheres the first barrier layer 22 to the skin, placing the exposed catheter end 12 within the domed interior region 16. The adhesive coating 32 forms a first, inner seal portion that impedes the passage of moisture into the interior protected region 16.

Likewise, the second moisture resistant barrier layer 24 includes a conventional adhesive coating 34 about the underside of its peripheral edge 20. The adhesive coating 34 adheres the second barrier layer 24 to the skin over the first barrier layer 22. The adhesive coating 34 forms a second, outer seal portion that impedes the passage of moisture toward the interior region 16.

As FIGS. 4 and 5 best show, the outer seal portion 34 is spaced from the inner seal portion 32. The spaced apart seal portions 32 and 34 form an open gap 36 between the seal portions 32 and 34. The intermediate gap 36 communicates with the upper interior region 26 that the moisture absorbing material 28 occupies. Preferably, the intermediate gap 36 is relatively small, being only about ⅛th inch in width.

Together, the seal portions 32 and 34 function as a single interrupted seal. The gap 36 that forms the interruption presents a relatively open, alternative fluid path to moisture that may leak through the outer seal portion 34. The absorbency of the material 28 serves further to wick or draw the moisture out of the gap 36, keeping it away from the inner seal portion 32. The presence of the gap 36 and the moisture absorbing material 28 divert unwanted moisture away from the interior protected region 16.

It should be appreciated that the gap 36 can be formed in various ways. The gap 36 could take the form of slots, holes, slits, or perforations formed in adhesive coatings 32 and 34 making up the seal area. In whatever form, the gap 36 serves as a means for diverting moisture into contact with the moisture absorbing material 28, instead of allowing it to proceed toward the interior protected region 16.

According to another aspect of my invention, at least a portion of the second moisture resistant barrier 24 is made of a light-transmissive material. This allows the user to see through the second barrier layer 24 into the pocket 26 occupied by the moisture absorbing material 28.

According to this aspect of my invention, the material 28 that occupies the visible pocket 26 further includes a moisture sensitive substance 38. The moisture sensitive substance 38 has a first visible characteristic when it is not in contact with moisture. The moisture sensitive substance 38 has a second, different visible characteristic when it is in contact with moisture.

For example, the moisture sensitive substance 38 may be clear or transparent when not in contact with moisture and then turn opaque when in contact with moisture. Alternatively, the moisture sensitive substance 38 may be one color when dry and another different color when moistened.

The user can easily see the changes in the visible characteristics of the moisture sensitive substance 38 through the light-transmissive outer barrier layer 24.

Various substances 38 can be used to impart different visual characteristics due to the presence or absence of moisture. For example, finely dispersed FDA-approved dyes can be used. These dyes preferably are present in highly concentrated form so that only small amounts of moisture would immediately produce noticeable color changes.

The first visible characteristic of the moisture sensitive substance 38 (for example, the color green) tells the user at a glance that no moisture has reached the gap 36 between the two seal regions 32 and 34. The protected region 16 occupied by the catheter end 12 is therefore also free of moisture.

The second visible characteristic of the moisture sensitive substance 38 (for example, the color red) immediately tells the user at a glance that moisture has at least breached the outermost seal portion 34 and has reached the gap 36. The user is forewarned that the protected region 16 of the barrier 10 is threatened. The user can take immediate steps to get away from the source of moisture and replace the barrier 10. This aspect of my invention will usually warn the user before unwanted moisture has breached the innermost seal region 32 and actually contacted the area 16 immediately surrounding catheter end portion 12.

In the illustrated and preferred embodiment, the material 28 containing the moisture sensitive substance 38 also absorbs moisture. In this way, the material 28 not only warns the user of the leakage of moisture, but also actively helps to combat the leakage.

Still, it should be appreciated that the material 28 occupying the pocket 26 between the inner and outer barrier layers 22 and 24 may be moisture absorbing, or moisture sensitive, or both.

FIGS. 6 to 9 show another moisture barrier 40 that incorporates the features of my invention. In many respects, the barrier 40 is like the barrier 10 shown in FIGS. 1 to 5. Common structural elements are assigned common reference numerals.

Like the barrier 10 shown in FIGS. 1 to 5, the barrier 40 includes an inner moisture resistant layer 22 and an outer moisture resistant layer 24. Each layer 22 and 24 has a peripheral edge, respectively 18 and 20, that includes an adhesive coating 32 and 34 to adhere the barrier 40 to the skin. As in FIGS. 1 to 5, the edges 32 and 34 are spaced apart to form inner and outer seal portions separated by a gap 36.

Like the barrier 10 shown in FIGS. 1 to 5, at least a portion of the outer layer 24 is light-transmissive. A moisture absorbing material 28 having a moisture sensitive substance 38 also occupies a pocket 26 between the inner and outer layers 22 and 24. The material 28 is visible through the light-transmissive portion of the outer layer 24 and contacts moisture that enters the gap 36. The material 28 displays different visible characteristics, depending upon the absence or presence of moisture in the gap 36, as previously described.

Unlike the barrier 10 shown in FIGS. 1 to 5, the barrier 40 shown in FIGS. 6 to 9 includes an antimicrobial material 42 in the interior protected region 16 that surrounds the catheter end portion 12.

Various constructions can be used. In the illustrated and preferred embodiment, the material 42 comprises a flexible foam or spongy pad holding betadine iodine. The material 42 could also comprise a gel form of betadine iodine, or other comparable antimicrobial material. It should be appreciated that the barrier 10 shown in FIGS. 1 to 5 could also employ an antimicrobial material 42 in the interior region 16.

Figure 6:
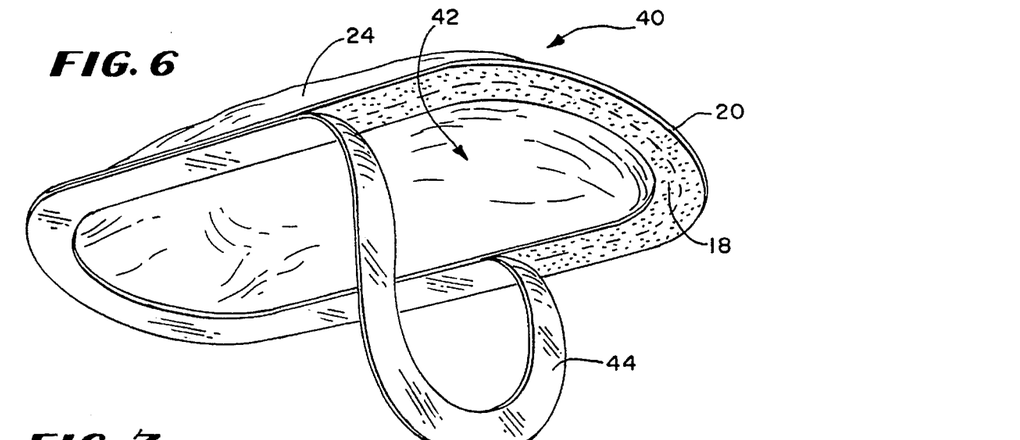
FIG. 6 is a perspective bottom view of another barrier that embodies my invention, showing the peel-away wrapper that covers the undersurface of the barrier before use.
Figure 7:
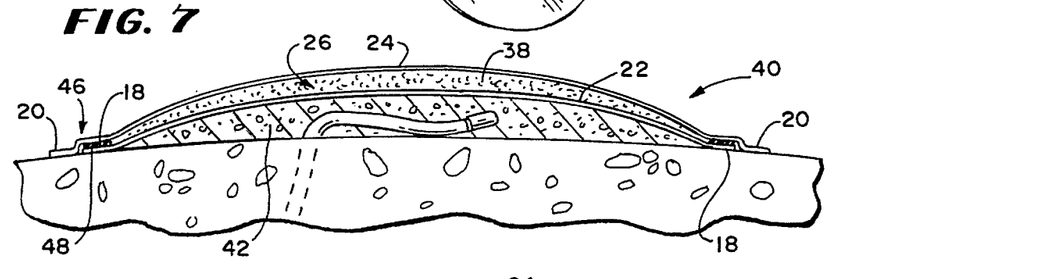
FIG. 7 is a side section view of the barrier shown in FIG. 6, which includes an antimicrobial material to surround the exposed catheter end.

The barrier 40 includes a peel away bottom liner 44 (see FIG. 6). The liner 44 prevents evaporation of the antimicrobial material 42 before use. The liner 44 also serves to protect the interior sterility and general cleanliness of the barrier 10 during storage and handling before use. The barrier 10 shown in FIGS. 1 to 5 is also preferably provided with a peel away bottom liner 44 (as FIG. 5 shows).

The barrier 40 shown in FIGS. 6 to 9 also includes means 46 for stiffening the inner sealing edge 18. By stiffening this interior edge 18, the user can apply more positive, uniform pressure upon the barrier 40 to form the inner seal portion 32. The moisture impeding capacity of the seal portion 32 is thereby increased.

Figures 8, 9:
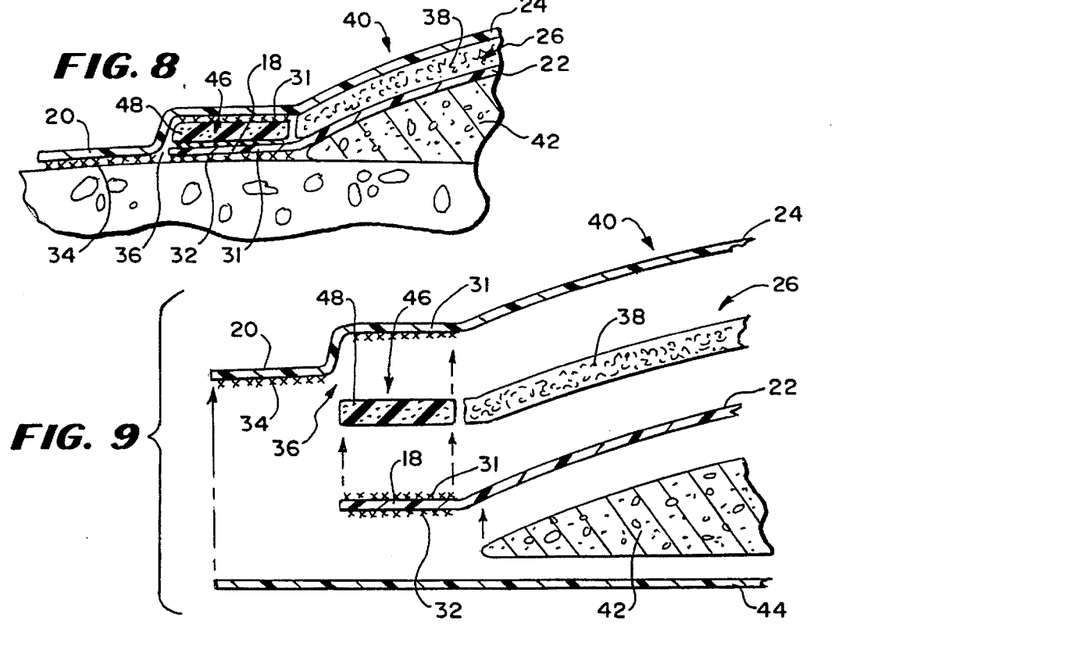
FIG. 8 is an enlarged view of the peripheral edge of the barrier shown in FIG. 7.
FIG. 9 is an enlarged exploded view of the peripheral edge of the barrier shown in FIG. 8.
Figure 10:
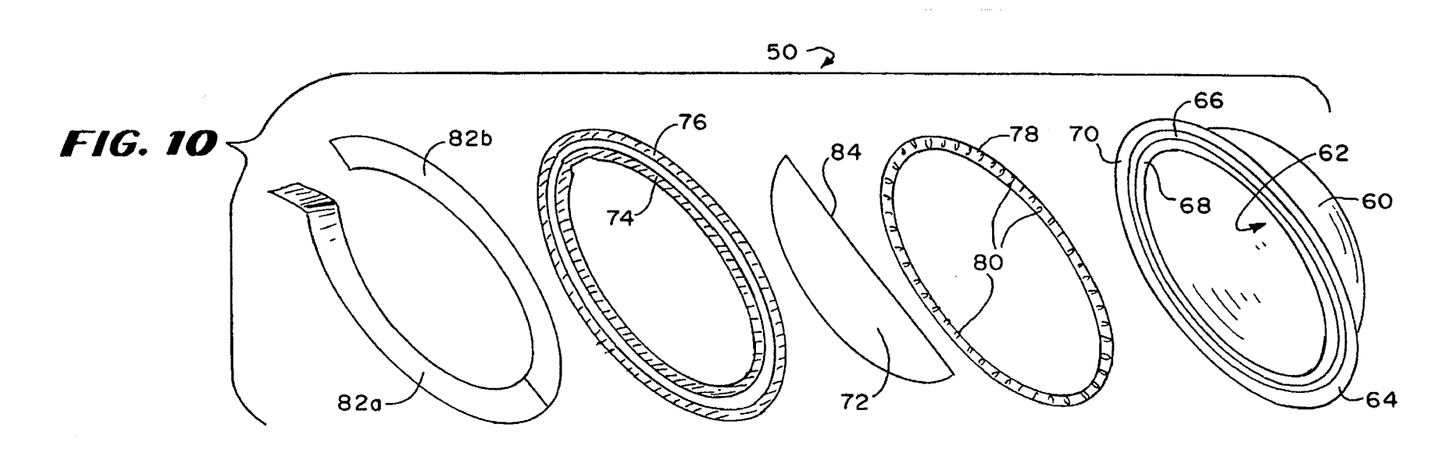
FIG. 10 is an exploded view of a shield for protecting an indwelling catheter that embodies the features of the invention.
Figure 11:
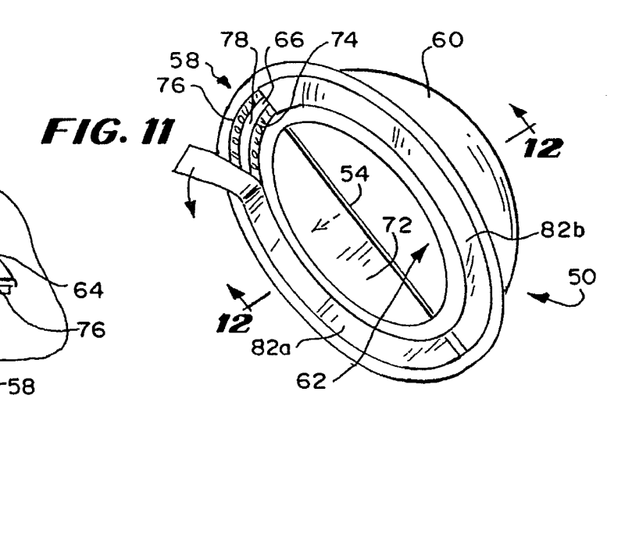
FIG. 11 is a perspective view of the shield shown in FIG. 10 when assembled.

The inner sealing edge 32 can be stiffened in various ways. In the illustrated embodiment, a ring 48 of material having a greater stiffness or rigidity than the material of the inner and outer layers 22 and 24 overlies the inner peripheral edge 18. Adhesive 31 joins the stiffening ring 48 to the upper surface of the edge 18 and the overlying portion of the outer layer 24 (as FIGS. 8 and 9 show).

The material forming the stiffening ring 48 is made of foam or is otherwise porous to conduct moisture from the gap 36 to the moisture absorbing material 28 in the manner previously described.

The drawings show the barriers 10 and 40 as preformed unitary bodies. This construction simplifies storage and use. Still, it should be appreciated that either barrier 10 or 40 can comprise separate barrier layers that could be individually stored and applied layer by layer at time of use.

FIGS. 10 to 13 show yet another moisture barrier 50 that incorporates the features of my invention. This barrier 50 is specially designed for the needs of a person who has an indwelling catheter, like one used for peritoneal dialysis, and who likes to participate in physical activities and water sports.

Figure 12:
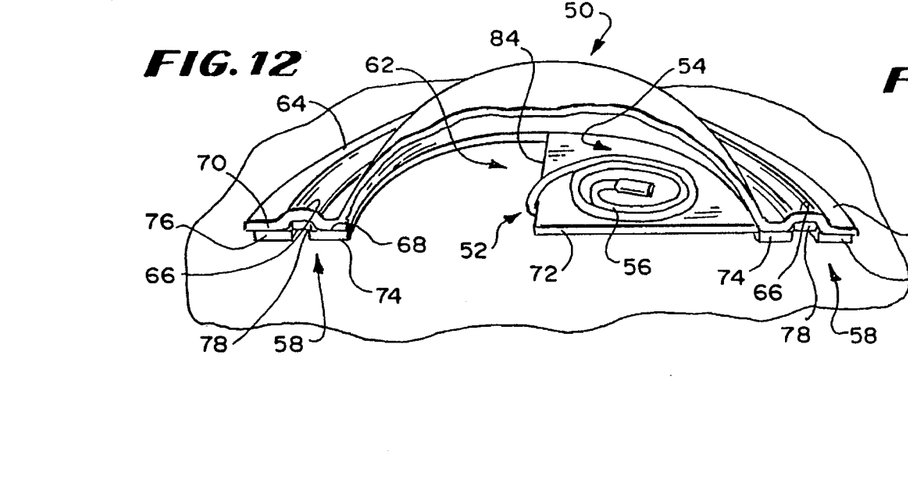
FIG. 12 is a cut-away perspective view of the shield shown in FIG. 10 when in use taken generally along line 12—12 in FIG. 11.

As FIG. 12 shows, in use, the barrier 50 covers the catheter site 52 and includes a receptacle or pocket 54 that stabilizes the catheter 56 in a secure, coiled position. This allows the person to engage in physical activity without soiling or contaminating the catheter site 52 or damaging the catheter 56 itself.

The barrier 50 also includes a seal structure 58 that keeps outside moisture from invading the pocket 54. This feature further frees the person to engage in water sports. In addition, the barrier 50 also displays a visible warning should moisture unexpectedly breach the seal structure 58. The warning appears before the moisture invades the catheter site 52.

To serve these multiple functions, the barrier 50 includes a generally rigid, moisture resistant outer shell 60. As FIGS. 10 to 13 show, the shell 60 is generally dome shaped, enclosing an open interior chamber 62. Still, other shapes could be used.

The shell 60 is preferably made from a molded plastic material.

The chamber 62 may be variously dimensioned, depending upon the size of the catheter 56 and the location of the catheter site 52. It has a horizontal width sufficient to cover the catheter exit site 52. It has a vertical height sufficient to accommodate the catheter 56 in a coiled condition (as FIG. 12 shows).

The shell 60 includes a peripheral lip 64 that carries the sealing structure 58. As FIG. 13 best shows, the lip 64 includes a raised groove 66 that divides the lip 64 into an inner sealing region 68 and an outer sealing region 70. When the chamber encircles the catheter exit site 52, the spaced sealing regions contact the skin surface (as FIG. 12 shows).

A panel 72 extends from one side of the interior sealing region 68 into the chamber 62. Preferably (as FIG. 11 best shows), the circumference of the panel 72 extends around about one-half of the periphery of the chamber 62. The panel 72, together with the overlying portion of the shell 60, forms the confines of the interior pocket 54 within the chamber 62.

In use (as FIG. 12 shows), the pocket 54 receives the catheter 56 in a compact, coiled conditioned. The pocket 54 retains the catheter 56 in this coiled condition within the chamber 62.

The inner and outer sealing regions 68 and 70 each includes an overlying adhesive ring, respectively 74 and 76. The adhesive rings 74 and 76 can comprise, for example, Double Coated Tape (Type 1522) made by 3M Corporation, as previously described. One adhesive side adheres the ring 74/76 to the associated sealing region 68/70. The other adhesive side of the ring 74/76 provides a moisture resistant coating that adheres the associated sealing region 68/70 to the skin.

In use, each ring 74/76 forms its own seal for keeping moisture out of the chamber 62, like the inner and outer seal portions 32 and 34 associated with the first described embodiment.

Figure 13:
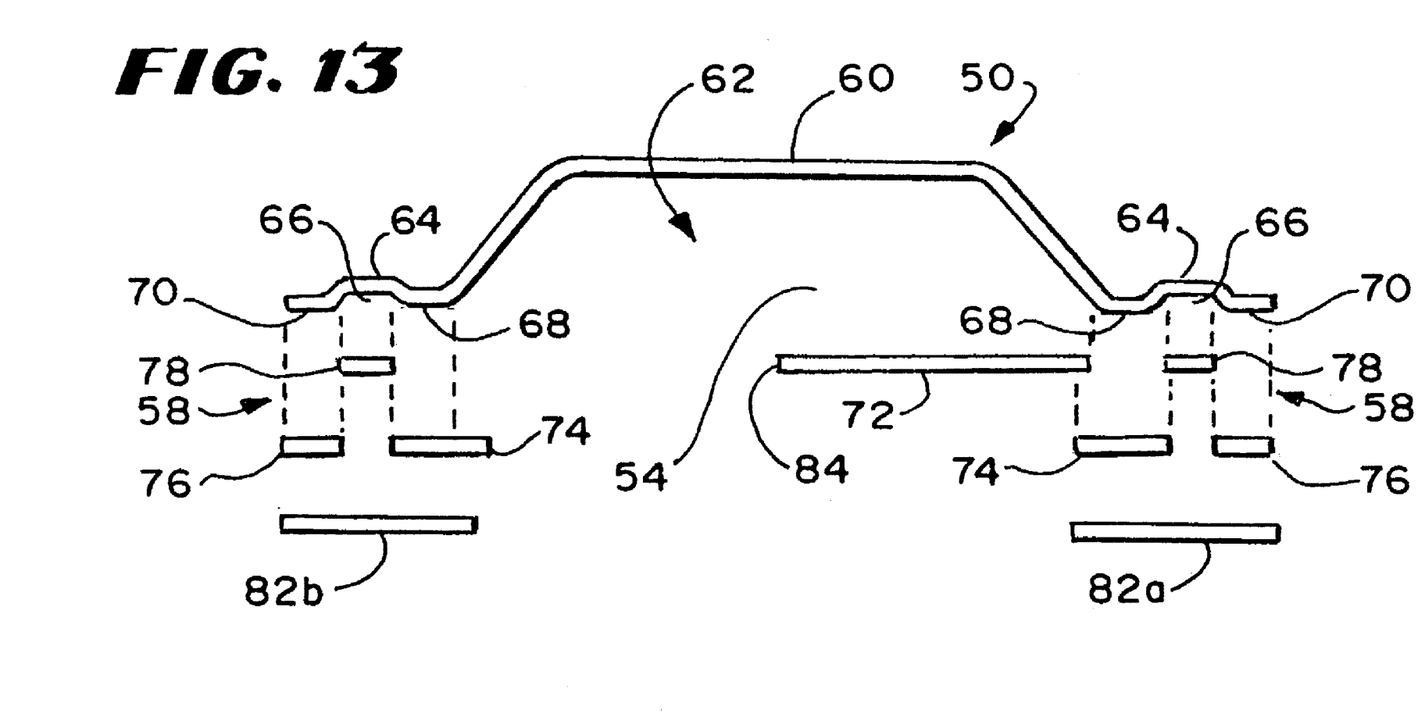
FIG. 13 is a side section view of the shield shown in FIG. 11.

A ring 78 of moisture absorbing material occupies the groove 66 between the inner and outer sealing regions 68 and 70 (see FIG. 13). The moisture absorbing ring 78 is preferably held in place by contact with the adhesive sides of the adjacent sealing rings 74 and 76 (as FIG. 13 also best shows). In an alternative embodiment, the moisture absorbing ring 78 can itself be secured by adhesive within the groove 66.

Together, the inner and outer sealing rings 74 and 76 function as a single interrupted sealing structure 58. The groove 66 that forms the interruption will be exposed to moisture only if there is a leak somewhere in the outer sealing ring 76. The absorbency of the ring 78 serves to retain the moisture, keeping it away from the inner sealing ring 74. In this way, unwanted moisture is kept out of the chamber 62.

Preferably, the shell 60 is made of a light-transmissive material, at least in the region of the groove 66. In this arrangement, the moisture absorbent ring 78 includes indicia 80 (see FIG. 10) that becomes visible when contacted by moisture. The indicia 80 are oriented to show through the light-transmissive material of the groove 66.

Thus, should water breach the outer sealing ring 76, its entry into the groove 66 will cause the indicia 80 of the moisture absorbing ring 78 to become visible. This serves to warn the user before the moisture further invades the inner sealing ring 74.

The sealing rings 74 and 76 are both preferably covered by an adhesive release liner 82 before use. The release liner 82 itself is also preferably divided into a lower half 82a and an upper half 82b. The lower half 82a of the release liner is generally coextensive with the circumference of the panel 72.

In use, the person first peels off the lower half of the release liner 82a. The person then locates the shell so that the interior edge 84 of the panel (forming the opening to the pocket 54) is just under the catheter exit site 52, with the pocket 54 facing the person. FIG. 12 generally shows this.

The person then brings the inner and outer sealing rings 74 and 76 uncovered by the removal of the lower release liner 82a into contact with his/her skin. This initially holds the shell 60 in position, freeing both hands to manipulate the catheter 56. The person coils the catheter 56 and tucks it into the pocket 54.

Once tucked away, the catheter 56 is retained in the pocket 54. The pocket 54 keeps the catheter 56 from uncoiling within the chamber 62. The pocket 54 holds the catheter 56 in a secure, stabilized position within the chamber 62.

Now, the person removes the top half of the release liner 82b and presses the entire lip region 64 into tight contact with the skin. The skin in this area may have to be shaved on some people to assure good adhesive contact.

Wearing the barrier 50, the person is free to engage in physical activities, even those resulting in contact with water. The barrier 50 protects the catheter 56 and exit site 52 from contamination and soiling. The barrier 50 also holds the catheter 56 in a secure position, protecting the catheter 56 from free movement and damage. The barrier 50 also normally protects the catheter 56 and exit site 52 from contact with moisture. If contact with moisture is threatened, the barrier 50 forewarns the person so that appropriate protective measures can be taken before exposure occurs.

The following claims set forth the features of my invention.

I claim:

1. A moisture barrier for an area exposed to moisture comprising:

a moisture resistant body having a generally light-transmissive portion and an interior region that is surrounded by a peripheral edge, means on the peripheral edge for adhering the body to the area while forming a seal for impeding the passage of moisture into the interior region, and moisture sensing means that is positioned for contact with moisture that penetrates the seal and that is visible through the generally light-transmissive portion of the body, the moisture sensing means displaying a first visible characteristic when out of contact with the moisture, thereby indicating that moisture has not penetrated the seal, and for displaying a second visible characteristic when in contact with the moisture, thereby indicating that the moisture has penetrated the seal.

2. A moisture barrier according to claim 1 wherein the moisture sensing means further serves to absorb the moisture penetrating the seal while displaying the second visible characteristic.

3. A moisture barrier according to claim 1 and further including an antimicrobial material in the interior region.

4. A moisture barrier according to claim 1 wherein the moisture sensing means comprises a material having a dye that displays the first visible characteristic when free of moisture and displays the second visible characteristic when contacted by moisture.

5. A moisture barrier according to claim 4 wherein the material further absorbs the contacting moisture.

6. A moisture barrier for an area exposed to moisture comprising:

an outer moisture resistant layer having a first peripheral edge that includes means for adhering the first edge to the area while forming an outer seal to impede the passage of moisture, and an inner moisture resistant layer below the outer moisture layer, the inner layer having a second peripheral edge that surrounds an interior region, the second peripheral edge including means for adhering the second edge to the area in series with the first edge while forming an inner seal in series with the outer seal to impede the passage of moisture, the second peripheral edge being spaced inwardly from the first peripheral edge to create a gap between the inner and outer seals, and moisture absorbing material located in the region between the inner and outer layers for absorbing moisture that enters the gap.

7. A moisture barrier for an area exposed to moisture comprising:

an outer moisture resistant layer having a generally light-transmissive portion and a first peripheral edge that includes adhesive means for adhering the first edge to the area while forming an outer seal to impede the passage of moisture, and an inner moisture resistant layer below the outer moisture layer in the region of the generally light-transmissive portion, the inner layer having a second peripheral edge that surrounds an interior region, the second peripheral edge including adhesive means for adhering the second edge to the area in series with the first edge while forming an inner seal in series with the outer seal to impede the passage of moisture, the second peripheral edge being spaced inwardly from the first peripheral edge to create a gap between the inner and outer seals, and moisture sensitive material located in the region between the inner and outer layers for contact with moisture that enters the gap, the moisture sensitive material being visible through the generally light-transmissive portion of the outer layer, the moisture sensitive material having a first visible characteristic when out of contact with moisture, thereby indicating the absence of moisture in the gap, and a second visible characteristic when in contact with moisture entering the gap, thereby indicating the presence of moisture in the gap.

8. A moisture barrier according to claim 7 wherein the moisture sensing material absorbs moisture entering the gap while displaying the second visible characteristic.

9. A moisture barrier according to claim 6 or 7 and further including an antimicrobial material in the interior region of the inner layer.

10. A moisture barrier according to claim 7 wherein the moisture sensing material includes a dye that displays the first visible characteristic when free of moisture and displays the second visible characteristic when contacted by moisture.

11. A moisture barrier according to claim 10 wherein the moisture sensitive material absorbs the contacting moisture.

12. A moisture barrier according to claim 6 or 7 and further including means for stiffening the second peripheral edge.

13. A moisture barrier according to claim 12 wherein the stiffening means comprises a body having a greater stiffness than the inner and outer layers and that is porous to moisture, the stiffening body overlying the second peripheral edge in the region between the inner and outer layers.

14. A moisture barrier for the exposed end of an indwelling catheter comprising moisture resistant barrier means that includes a generally light-transmissive portion, the barrier means defining an interior region that is shaped to cover the exposed catheter end, the barrier means including adhesive means for adhering the barrier means to the skin over the exposed catheter end while forming seal means for impeding the passage of moisture into the interior region, moisture sensing means visible through the generally light-transmissive portion of the barrier means for contact with moisture that penetrates the seal means, the moisture sensing means displaying a first visible characteristic when out of contact with the moisture, thereby indicating that moisture has not penetrated the seal means, and for displaying a second visible characteristic when in contact with the moisture, thereby indicating that the moisture has penetrated the seal means.

15. A moisture barrier according to claim 14 wherein the moisture sensing means further absorbs moisture while displaying its second visible characteristic.

16. A moisture barrier for the exposed end of an indwelling catheter comprising a first moisture resistant barrier defining a first interior region that is shaped to cover the exposed catheter end, the first barrier including adhesive means about its peripheral edge for adhering the first barrier to the skin over the exposed catheter end while forming a first seal to impede the passage of moisture into the interior region, a second moisture resistant barrier defining a second interior region that is shaped to cover the first moisture resistant barrier, the second moisture resistant barrier including a light-transmissive portion, the second moisture resistant barrier including adhesive means about its peripheral edge for adhering the second barrier to the skin over the first barrier while forming a second seal spaced outwardly from the first seal to impede the passage of moisture from the exterior toward the first seal, and a moisture sensitive material located between the first and second barriers for contact with moisture that enters the region between the first and second seals, the moisture sensitive material being visible through the generally light-transmissive portion of the second barrier, the moisture sensitive material having a first visible characteristic when out of contact with moisture, thereby indicating the absence of moisture in the region between the two seals, and a second visible characteristic when in contact with moisture entering the region, thereby indicating the passage of moisture in the region between the two seals.

17. A moisture barrier according to claim 16 wherein the moisture sensing material absorbs moisture entering the region between the two seals gap while displaying the second visible characteristic.

18. A moisture barrier according to claim 16
and further including a material in the interior region that surrounds the exposed catheter end and that includes an antimicrobial substance.

19. A moisture barrier according to claim 16 wherein the moisture sensing material includes a dye that displays the first visible characteristic when free of moisture and displays the second visible characteristic when contacted by moisture.

20. A moisture barrier according to claim 19 wherein the moisture sensitive material absorbs moisture.

21. A moisture barrier according to claim 16
and further including means for stiffening the peripheral edge of the first barrier.

22. A moisture barrier according to claim 21 wherein the stiffening means comprises a body having a greater stiffness than the first and second barriers and that is porous to moisture.

23. A moisture barrier for the exposed end of an indwelling catheter comprising:
an outer moisture resistant layer having a first peripheral edge that includes means for adhering the first edge to the area while forming an outer seal to impede the passage of moisture, and
an inner moisture resistant layer below the outer moisture resistant layer, the inner layer having a second peripheral edge that surrounds an interior region that accommodates the exposed catheter end, the second peripheral edge including means for adhering the second edge to the area in series with the first edge while forming an inner seal in series with the outer seal to impede the passage of moisture, the second peripheral edge being spaced inwardly from the first peripheral edge to create a gap between the inner and outer seals, and
moisture absorbing material located in the region between the inner and outer layers for absorbing moisture that enters the gap.

24. A moisture barrier according to claim 23
and further including means for stiffening the second peripheral edge.

25. A moisture barrier according to claim 24 wherein the stiffening means comprises a body having a greater stiffness than the inner and outer layers and that is porous to moisture.

26. A moisture barrier for the exposed end of an indwelling catheter comprising
moisture resistant barrier means that includes a peripheral lip having a generally light-transmissive portion, the barrier means defining an interior region that is shaped to cover the exposed catheter end,
adhesive means on the lip for adhering the barrier means to the skin over the exposed catheter end while forming seal means for impeding the passage of moisture into the interior region, and
moisture sensing means on the lip visible through the generally light-transmissive portion for contact with moisture that penetrates the seal means, the moisture sensing means displaying a first visible characteristic when out of contact with the moisture, thereby indicating that moisture has not penetrated the seal means, and for displaying a second visible characteristic when in contact with the moisture, thereby indicating that the moisture has penetrated the seal means.

27. A moisture barrier according to claim 26
and further including means defining a pocket within the interior region for holding the exposed end of the indwelling catheter.

28. A moisture barrier according to claim 26 wherein the seal means includes an outer seal region on the lip spaced from the interior region and an inner seal region on the lip next to the interior region, and
wherein the moisture sensing means is positioned between the inner and outer seal regions.

29. A moisture barrier for the exposed end of an indwelling catheter comprising
moisture resistant barrier means that includes a peripheral lip having a generally light-transmissive portion, the barrier means defining an interior region that is shaped to cover the exposed catheter end,
adhesive means on the lip for adhering the barrier means to the skin over the exposed catheter end while forming seal means for impeding the passage of moisture into the interior region, and
means defining a pocket within the interior region for holding the exposed end of the indwelling catheter in a coiled condition, wherein the seal means includes an outer seal region on the lip spaced from the interior region and an inner seal region on the lip next to the interior region, and further including moisture absorbing means positioned between the inner and outer seal regions.

30. A moisture barrier according to claim 29 wherein the seal means includes an outer seal region on the lip spaced from the interior region and an inner seal region on the lip next to the interior region,
and further including moisture sensing means positioned between the inner and outer seal regions.

* * * * *